(12) United States Patent
Schwartz et al.

(10) Patent No.: US 9,091,630 B2
(45) Date of Patent: Jul. 28, 2015

(54) NANOSENSORS AND METHOD OF MANUFACTURE

(71) Applicant: Lockheed Martin Corporation, Bethesda, MD (US)

(72) Inventors: Rebecca Schwartz, Chester Springs, PA (US); John Arthur Wood, Bethlehem, PA (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 14/245,571

(22) Filed: Apr. 4, 2014

(65) Prior Publication Data

US 2014/0302595 A1    Oct. 9, 2014

Related U.S. Application Data

(60) Provisional application No. 61/808,466, filed on Apr. 4, 2013.

(51) Int. Cl.
*G01N 15/06* (2006.01)
*G01N 33/00* (2006.01)
*G01N 33/48* (2006.01)
*G01N 27/12* (2006.01)

(52) U.S. Cl.
CPC .................................. *G01N 27/127* (2013.01)

(58) Field of Classification Search
USPC .......................... 422/50, 83, 98, 82.01, 82.02
See application file for complete search history.

(56) References Cited

U.S. PATENT DOCUMENTS

| | | | |
|---|---|---|---|
| 8,313,633 B2 * | 11/2012 | Li et al. .......................... | 205/183 |
| 8,795,359 B2 * | 8/2014 | Boyden et al. ..................... | 623/8 |
| 8,810,417 B2 * | 8/2014 | Hood et al. .................... | 340/603 |

* cited by examiner

*Primary Examiner* — Brian J Sines
(74) *Attorney, Agent, or Firm* — Oblon, McClelland, Maier & Neustadt, L.L.P.

(57) ABSTRACT

A nanosensor and methods to manufacture are disclosed. For example, a detection system for detecting the presence of a target substance can include a nanosensor that includes a sensing layer, and a plurality of sockets embedded within the body of the sensing layer, each socket having a physical profile matching a shape of the target substance such that, when target substances occupy the sockets, at least one measurable physical characteristic of the sensing layer changes.

7 Claims, 7 Drawing Sheets

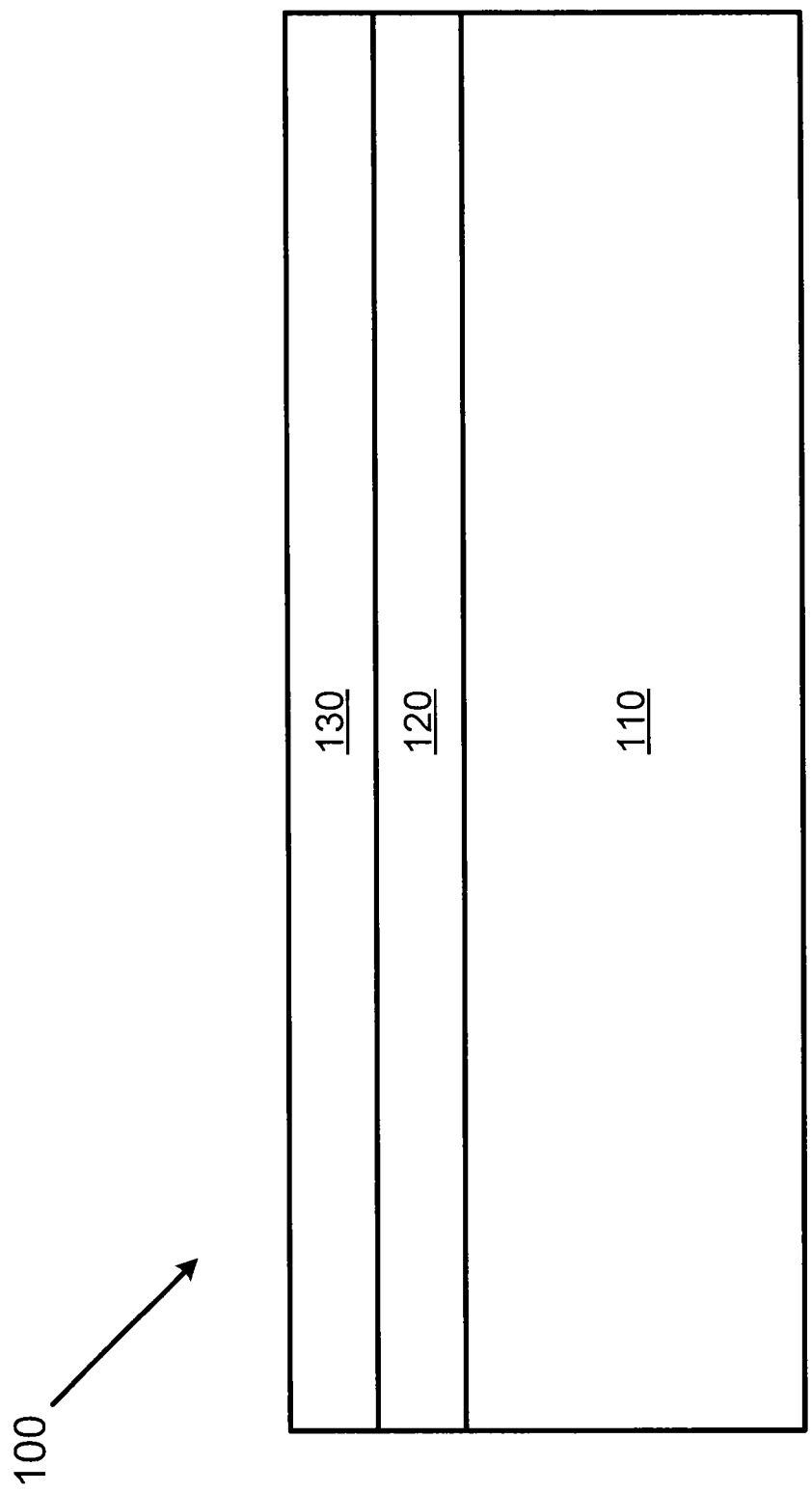

NANOSENSORS AND METHOD OF MANUFACTURE

INCORPORATION BY REFERENCE

This application claims the benefit of U.S. Provisional Application No. 61/808,466 entitled "CHEMICAL AND BIOLOGICAL SENSOR FABRICATION USING NANOIMPRINT LITHOGRAPHY AND SOCKET CREATION" filed on Apr. 4, 2013, the content of which is incorporated herein by reference in its entirety.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

Generally, chemical sensors need both selectivity, i.e., the ability to accurately discern one substance from another, and sensitivity. Nanotechnology provides the possibility of producing compact, highly sensitive, compound-specific chemical sensors. However, producing a nanosensor that incorporates the requisite selectivity and sensitivity is potentially very challenging because, as a general rule, the physical traits of a sensor that promote selectivity and sensitivity tend to work against each other.

SUMMARY

Various aspects and embodiments of the invention are described in further detail below.

In an embodiment, a detection system for detecting the presence of a target substance includes a nanosensor that includes a sensing layer, and a plurality of sockets embedded within the body of the sensing layer, wherein each socket includes a plurality of socket members and each socket has a physical profile matching a size and shape of at least a portion of the target substance, and polarity if appropriate for the selected target substance, such that, when target substances occupy the sockets, at least one measurable physical characteristic of the sensing layer changes.

In another embodiment, a method for manufacturing a detection system for detecting the presence of a target substance includes forming a nanosensor that includes a sensing layer, and forming a plurality of sockets incorporated within and/or on a surface of the body of the sensing layer, wherein each socket includes a plurality of socket members and each socket has a physical profile matching a size and shape of at least a portion of the target substance, and polarity if appropriate for the selected target substance, such that, when target substances occupy the sockets, at least one measurable physical characteristic of the sensing layer changes.

BRIEF DESCRIPTION OF THE DRAWINGS

Various embodiments of this disclosure that are proposed as examples will be described in detail with reference to the following figures, wherein like numerals reference like elements, and wherein:

FIG. 1 is a side view of an example nanosensor.

DETAILED DESCRIPTION OF EMBODIMENTS

Figure 2A:
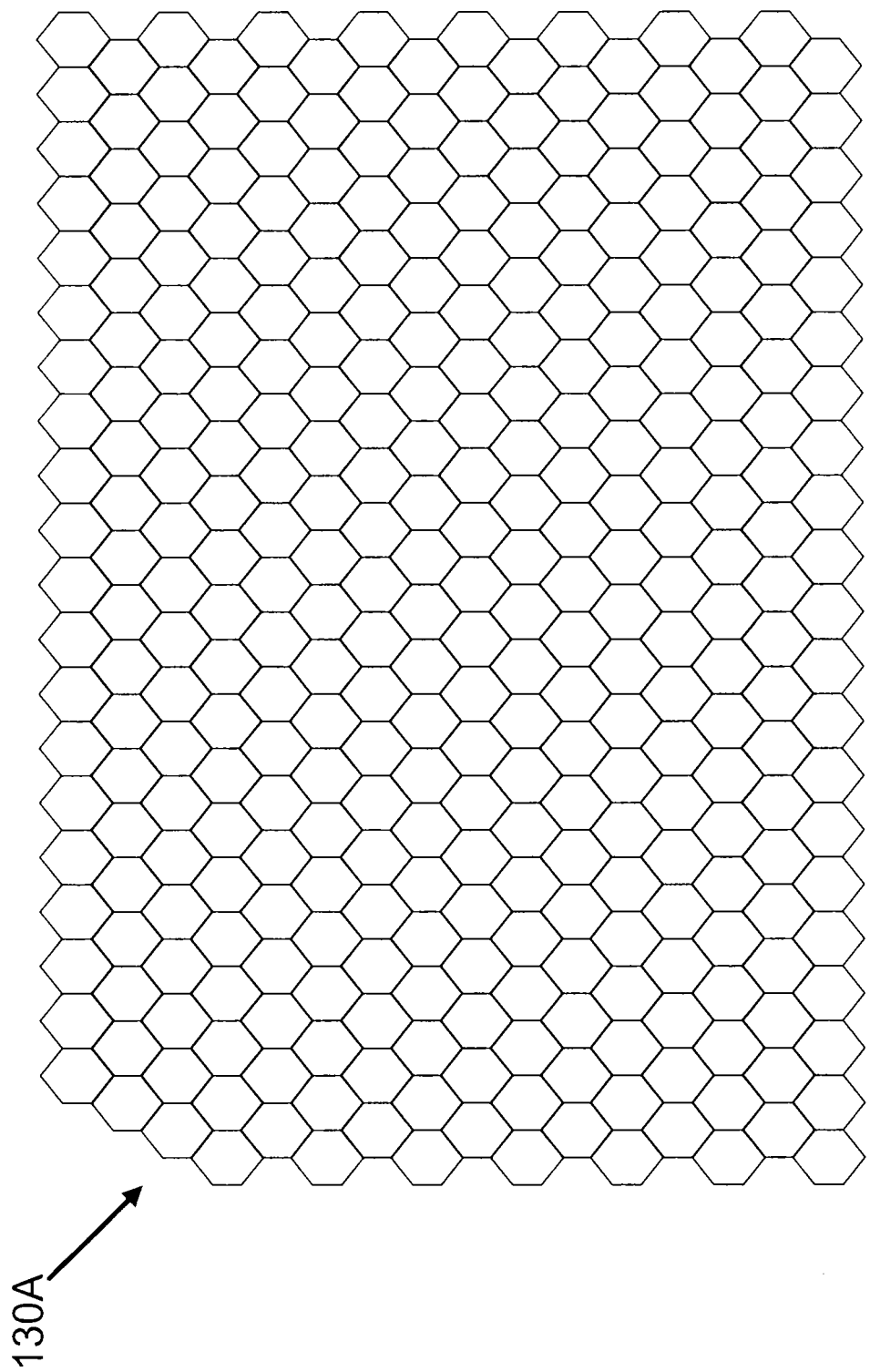
FIGS. 2A-2D are plan views depicting the manufacture of sockets for the example nanosensor of FIG. 1.

The disclosed methods and systems below may be described generally, as well as in terms of specific examples and/or specific embodiments. For instances where references are made to detailed examples and/or embodiments, it is noted that any of the underlying principles described are not to be limited to a single embodiment, but may be expanded for use with any of the other methods and systems described herein as will be understood by one of ordinary skill in the art unless otherwise stated specifically.

FIG. 1 is a side view of an example nanosensor 100. As shown in FIG. 1, the nanosensor 100 includes a substrate 110, an optional intermediate layer 120 and a sensing layer 130.

The substrate 110 can be any of a large variety of non-conductive or semi-conductive materials, such as silicon, diamond, sapphire, germanium, and silicon carbide. Alternatively, the substrate 110 can be any of a large variety of metals, such as copper, silver and gold of a single metal crystal of a known crystal orientation. The nature of the substrate 110 may lend itself to manufacturing ease, for sensing functionality and/or for mechanical support. Depending on the circumstances and design goals, the substrate 110 may not be necessary.

The intermediate layer 120 for the example of FIG. 1 is boron nitride heated and annealed so as to form a hexagonal matrix, which can provide an electrically insulating layer with a similar lattice structure for graphene to lay upon thus better exploiting graphene's inherent properties. However, in other embodiments some other material(s) may be applied depending on the nature and composition of the sensing layer 130. Further, in other embodiments, the intermediate layer 120 may be eliminated. For example, if the substrate 110 is made from silica and the sensing layer 130 is graphene, the intermediate layer 120 may be eliminated. Similarly, if the sensing layer 130 is made from another suitable material other than graphene, the intermediate layer 120 may be eliminated.

The composition of the intermediate layer 120 may also change dependent on a type of sensing used. By way of example, if the sensing is done using other than electrical characteristics, such as x-ray fluorescence, infrared, Raman or Terehertz sensors, a conducting substrate such as copper can be used. By way of another example, the intermediate layer 120 may be composed of copper if surface waves were employed to do the sensing, but not if overall resistance change is to be measured. Normally, an insulating substrate is needed if a change in resistance of the sensor layer 130 is used to detect the target substance.

The sensing layer 130 for the example of FIG. 1 is made of a graphene sheet having a thickness of a single molecule. However, in other embodiments the sensing layer 130 may use multiple sheets of molecule-thick graphene, or a graphene composite being more than a single molecule thick. Still further, it is to be appreciated that, in a variety of embodiments, substances other than graphene may be used depending on the desired physical traits of the sensing layer 130. That is, the type of material and thickness of the sensing layer 130 will depend on the type of substance/molecule sensed (hereinafter, the "target substance") and the method for sensing the presence of targeted molecules/substances, such as measuring changes in conductivity, measuring changes in optical transmission properties, measuring changes in resonance (e.g., resonant frequency and/or system Q), and so on.

For the purposes of this disclosure there are two major divisions of "socket" production, one for small molecules/substances, and one for large molecules/substances.

Figure 2B:
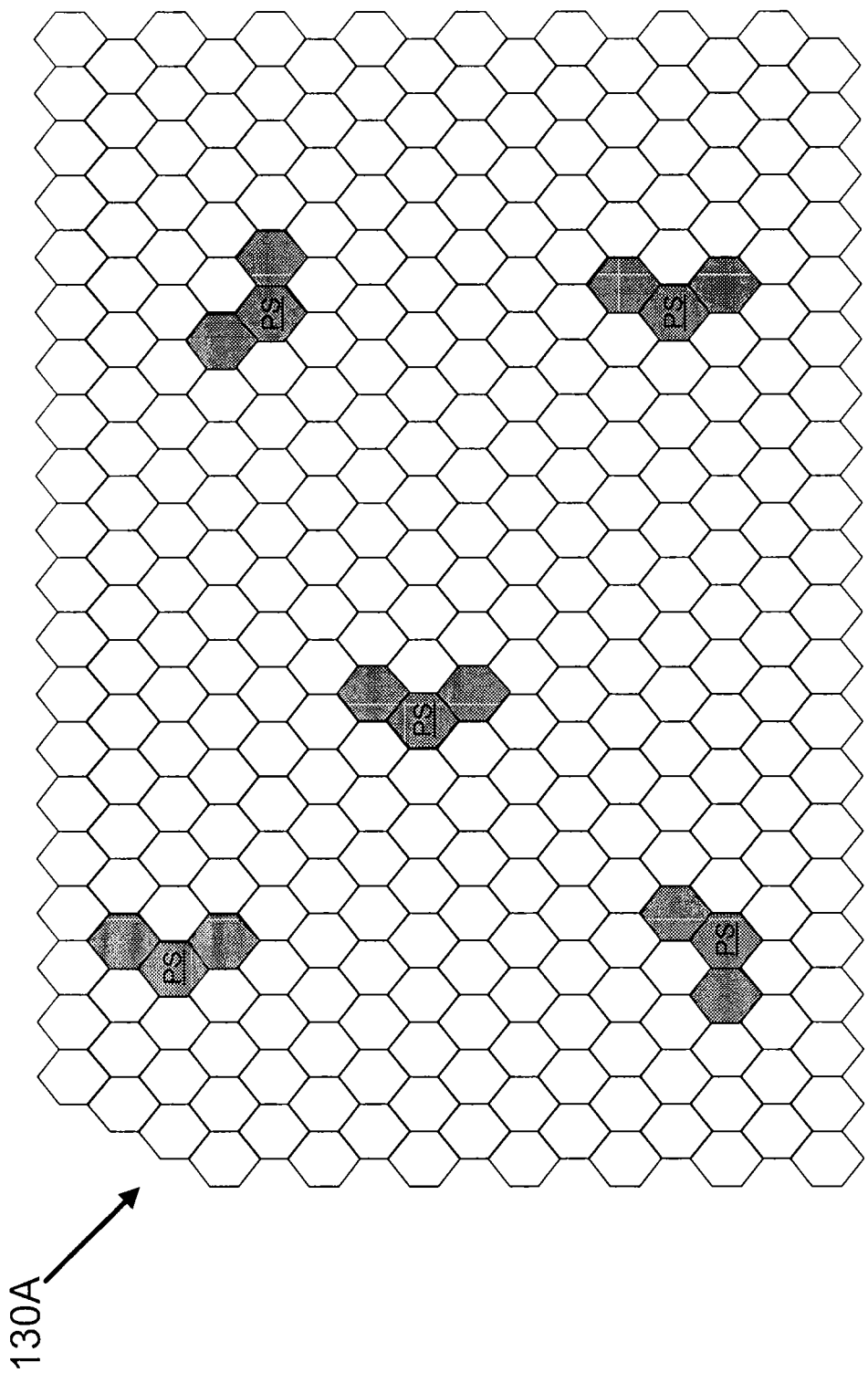

FIGS. 2A-2B depict plan (top-down) views of an exemplary sensing layer portion 130A of the sensing layer 130 of FIG. 1 as it is populated with small-molecule sockets. As shown in FIG. 2A, the sensing layer portion 130A, which in this embodiment consists of a molecule-thick layer of graphene, has a hexagonal molecular structure. While not shown in FIG. 2A, an ultraviolet interference pattern can be projected onto the sensing layer portion 130A to make some areas relatively hot and other areas relatively cool. It is in the cool areas where sockets formation will occur. Accordingly, fine placement control of individual sockets may be achieved according to a grid pattern.

For large target molecules/substances, individual segments of a socket member may attach to graphene more strongly than does the target substance as a whole. Accordingly, one can place first (partial) socket members PS in a grid placement on the (graphene) sensing layer portion 130A by selecting conditions such that the socket members can only adsorb onto the sensing layer at predetermined locations. As an example, an interference pattern of ultraviolet light could produce a grid of hot and cold spots on the sensor surface, allowing the socket member to adsorb onto the sensor surface at only the cold spots.

Sockets may be formed within the sensing layer 130 or atop the sensing layer 130. Typically, sockets will have at least two distinct members that comprise the sockets. FIG. 2B depicts a first of two socket members PS placed according to a grid pattern. The first socket members PS are exposed to the target substance, while maintaining conditions that prevent the adsorption of the target substance on the background sensor surface, but do allow attachment to the partial socket members. The attachment is accomplished by a combination of shape and van der Waals attraction of atoms within the partial socket and target substance that have complimentary partial electrical charges.

Once all excess socket member materials are removed from the area of the sensing layer portion 130A, a second socket portion can be formed onto the sensing layer portion 130A as will be further discussed below. The second socket members are designed so that they attach to the free side of the target substance, but do not 'sit down' on the sensing layer portion 130A (to avoid placement anywhere except at the half-socket/target substance locations).

Figure 2C:
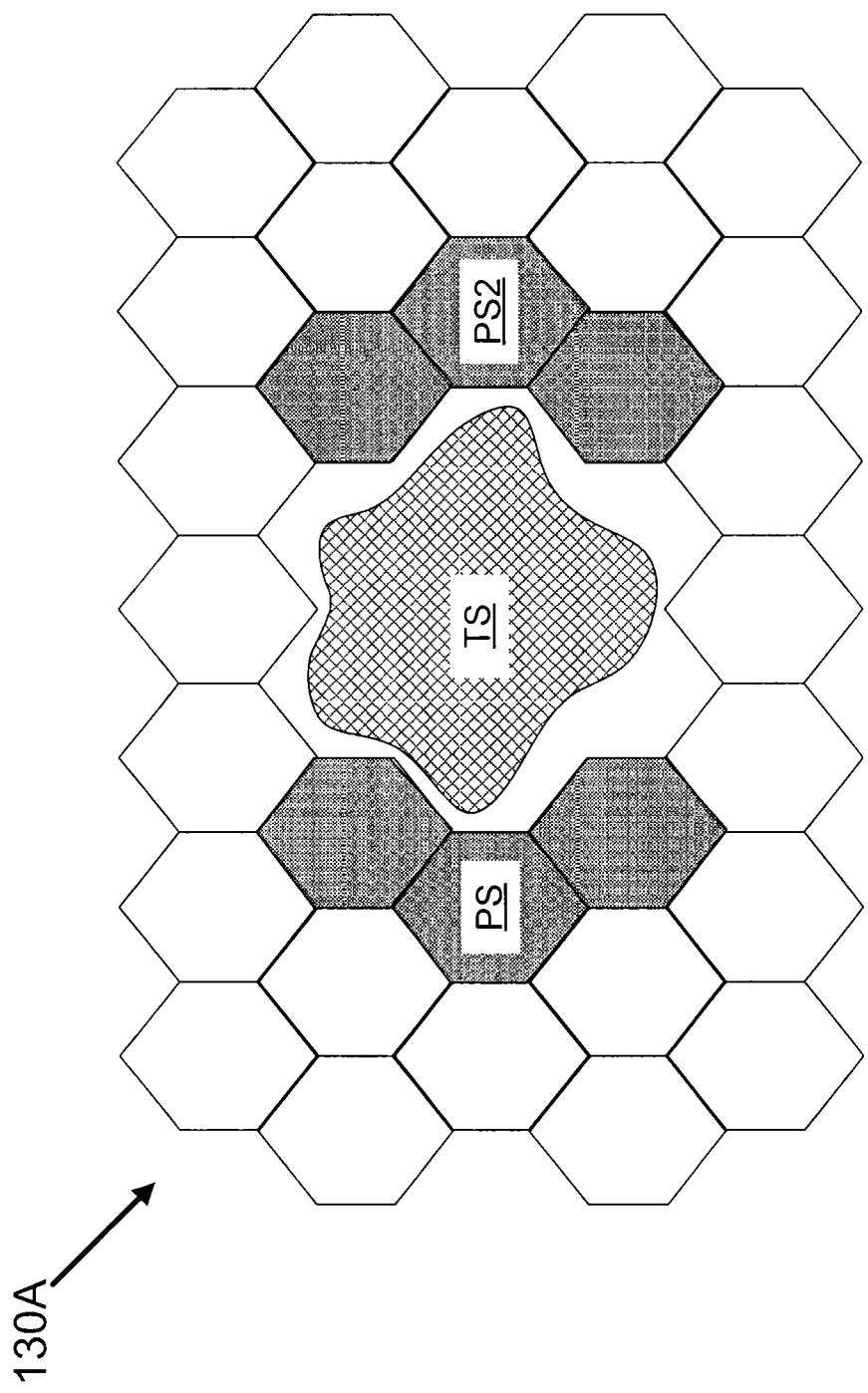
Figure 2D:
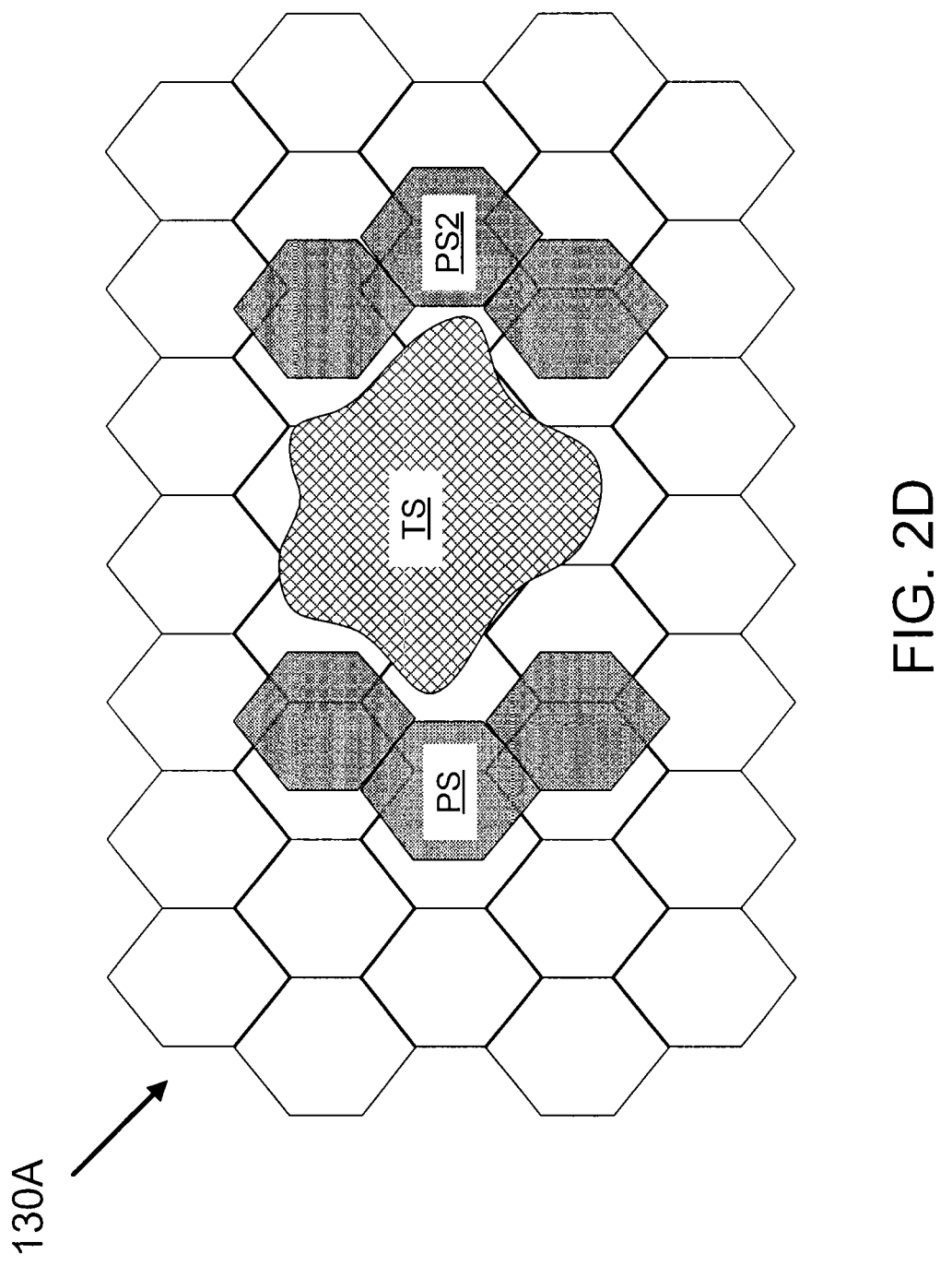

FIG. 2C depicts a plan view of socket members {PS, PS2} that are embedded within the sensing layer portion 130A with a target substance TS represented between the socket members {PS, PS2}. FIG. 2D depicts an example where the sockets {PS, PS2} are formed atop the sensing layer portion 130A with a target substance TS represented between the socket members {PS, PS2}. In the example of FIG. 2D, the socket members {PS, PS2} are depicted as being askew/not aligned with the hexagonal matrix of the (graphene) sensing layer portion 130A. This is because energetically it is unlikely that the atoms of a partial socket would align directly atop of the atoms of a graphene layer.

For both the examples of FIG. 2C and FIG. 2D, the target substance TS is attracted to the socket members {PS, PS2} by van der Waals forces, which as known in the relevant arts are not hard covalent bonds (such as those that bind the socket molecules together), but more distant associations that hold the socket parts to the graphene, and which hold the target substance in a socket.

In addition to the use of interferometric methods for location placement, magnetic fields and/or chemical tethers may be applied to the substrate and/or to the partial sockets to assist with molecular location and orientation. For the purpose of this disclosure, a "chemical tether" is any chemical compound or element that can attract or attach itself to a particular portion of a molecule to assist in orienting and placing the partial socket or target substance upon a sensing layer. Typically, each socket will employ one or more (usually two) separate chemical tethers. For example, the chlorine atom in the target substance chlorobenzene can use a heteroatom, such as nitrogen in the socket, as a tether because the partial positive charge of the nitrogen attracts chlorine's partial negative charge. In some embodiments, the spacing and/or orientation of individual sockets may be random. However, in other embodiments it is envisioned that the spacing of individual sockets may be uniform and/or the orientation of sockets be made common to the extent practical, necessary, or otherwise desirable. In still other embodiments, however, it may be advantageous that socket orientation occur such that angular orientation differs according to physical position. For example, it may be desirable to orient sockets according to a sine wave as a function of distance. Other orientations may take the form of a Guassian function, a radial orientation, and so on. That is, socket orientation can be determined on a case-by-case basis according to desirable design parameters, and is not limited to any example disclosed herein. In another scenario, where specificity would be sufficiently satisfied through shape and size then nano-imprinting or nano-stamping can be used for the fabrication, and a chemical tether as mentioned above would not be required.

Returning to FIG. 2D, once the loosely-held second socket member PS2 is in place, chemical reactions are implemented that remove the functional groups that prevented the second socket member PS2 from attaching to the surface of the sensing layer portion 130A, and allow the second socket member PS2 to 'sit down' on the sensing layer portion 130A and be held by van der Waals forces, completing the socket.

Then the sensing layer portion 130A is heated sufficiently to release the target substance from the sockets 210, and the sockets 210 are ready to be used.

There need be no tradeoff between sensitivity and selectivity given a combination of the size, shape and locations of the polar elements on the socket produce selectivity.

For large target substances, the target substance may be attracted more strongly to a graphene (or other material) surface than any one partial socket. In this case, there are several approaches to the creation of sockets.

In a first non-limiting approach, the target substances are adsorbed in the grid formation onto a graphene surface, and the socket members added, one by one, in the same manner as the second socket member in the case of small molecules. However, from the second socket member on, the socket members will attach not only to the target substance, but also to the other socket member based upon complementary functional groups, forming a strongly interlinked socket that as a whole adsorbs to graphene more strongly than does the target substances as a whole. In another non-limiting approach, a socket can be manufactured around a target substance on a substrate other than graphene, desorbed as a whole and then adsorbed onto graphene as a combination socket-target. Then the target substance can be desorbed from the graphene-socket surface in preparation for using the sensor.

Because different chemical compounds will have different physical and electrical field shapes, the sockets 210 are formed such that the target substances (or specific portions thereof) should precisely fit within the sockets, matching the required size, shape and electrical field conformation. For example, the sockets 210 can be made into the shape and size of a chlorobenzene molecule, an odorizing taggant chemical (or other volatile residue), drugs or drug metabolites (e.g., benzoylecgonine), and so on. In addition to sensing a single compound, the sockets 210 can be manufactured so as to receive a class of compounds.

By way of further example in the case where a biological detector is desired, the sockets 210 can be made in the form of a target virus or in the shape of volatile waste products, which can be an indication of food contamination, infections or other issues. For instance, botulism bacteria produce waste products that could be sensed using the disclosed methods and systems.

Figure 3:
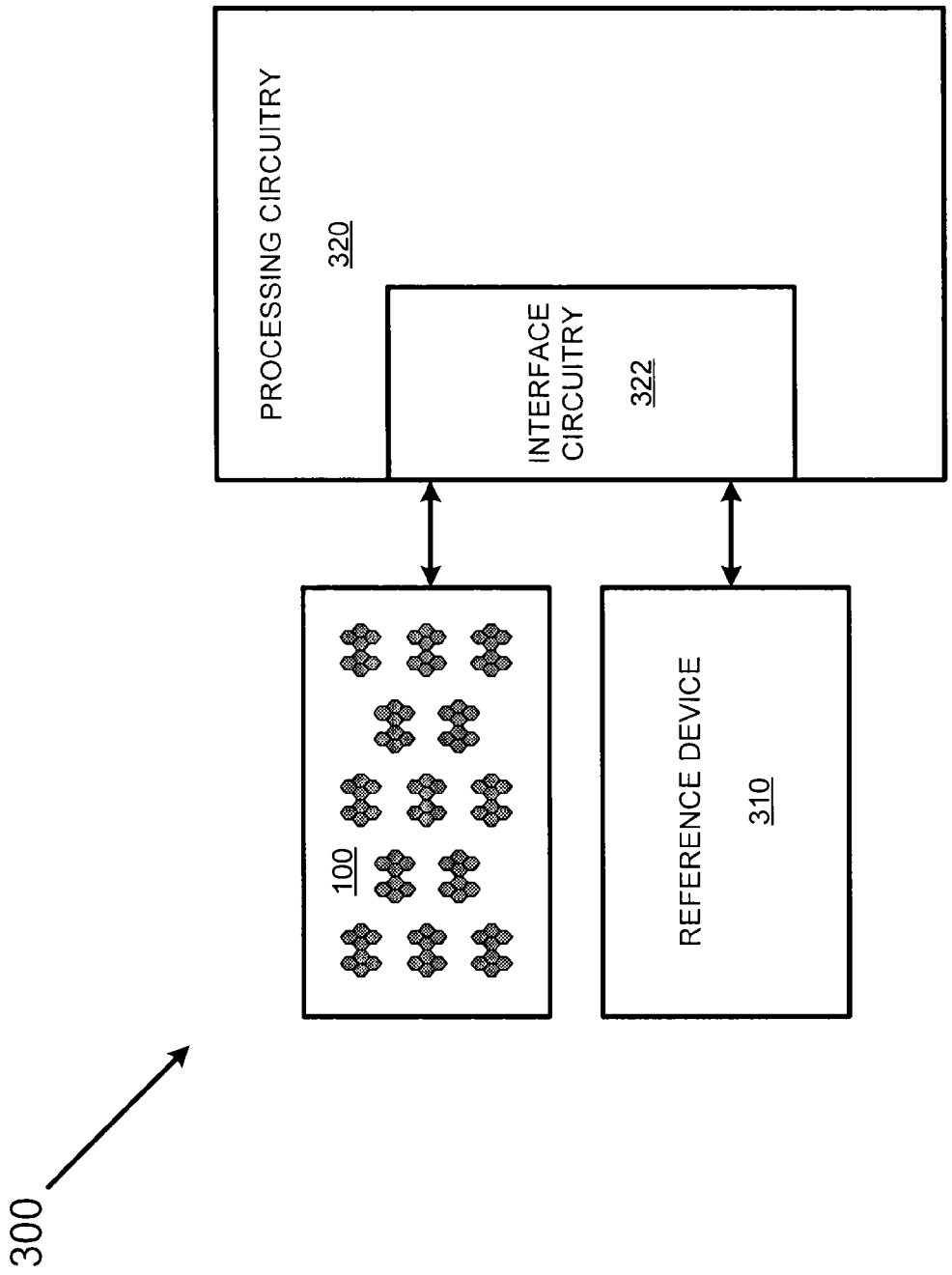
FIG. 3 depicts an example nanosensor and reference device used in a sensing system.

FIG. 3 depicts an example nanosensor-based sensing system 300. As shown in FIG. 3, the sensing system 300 includes a nanosensor 100, an optional reference device 310 and a processing system 320 having a set of interface electronics 322 usable to monitor the sensor 100 and reference device 310.

Generally, the reference device 310 can take the form of the sensor 100 with or without sockets. Assuming that similar processing is used on both the sensor 100 and the reference device 310, the reference device 310 should react in similar ways to the sensor 100 with respect to temperature, aging and other environmental conditions. If the reference device 310 incorporates sockets, such sockets should be sealed such that contamination by target substances is prohibited.

Assuming that the sensor 100 is configured to change resistance upon exposure to a target substance, the sensor 100 and the reference device 310 can be, for example, configured in the form of a resistor bridge such that the processing device 320 can measure changes in output voltage between the sensor 100 and the reference device 310.

Assuming that the sensor 100 is manufactured so as to be well characterized, the reference device 310 can be eliminated. Similarly, if the processing device 320 can be calibrated to individual sensors, the reference device 310 can be eliminated.

Other forms of sensing may require more sophisticated interface electronics and processing. By way of example, if the resonant characteristics of the sensor 100 change upon exposure to a target substance, the interface circuitry 322 can take the form of a pair of oscillator driving circuits using the sensor 100 and reference device 310 to determine frequency and/or system quality Q, where after the processing circuitry 322 can measure differences in frequency output. Other prospective physical changes, such as capacitance and optical transmission qualities, will require an appropriately configured interface circuitry 322.

Figure 4:
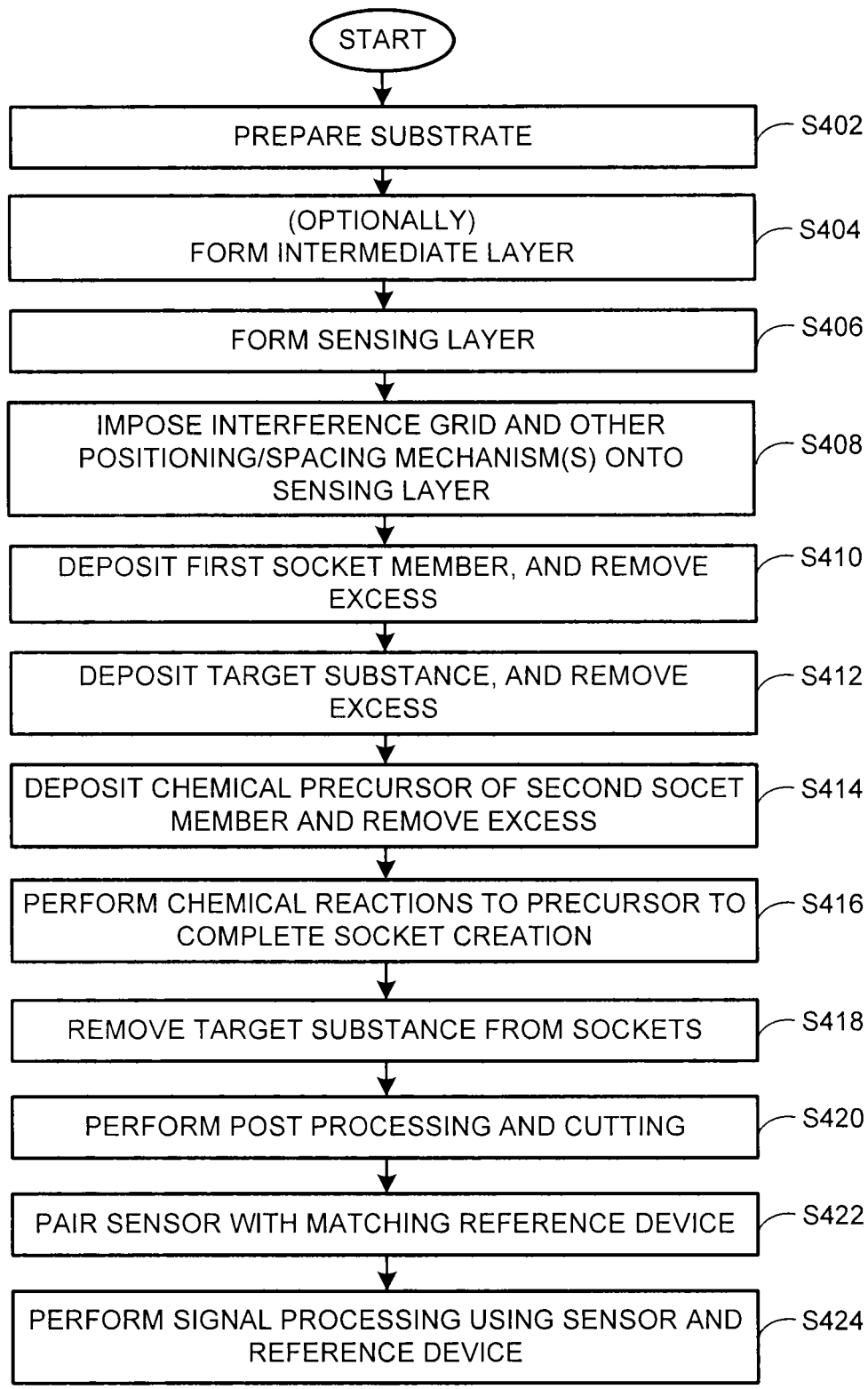
FIG. 4 is a flowchart outlining an example set of operations usable to produce and use the nanosensor of FIGS. 1-3 above.

FIG. 4 is a flowchart outlining an example set of operations usable to produce and use the nanosensor of FIGS. 1-3 above. While the below-described steps are described as occurring in a particular sequence for convenience, it is noted that the order of various operations may be changed from embodiment to embodiment. It is further noted that various operations may occur simultaneously or may be made to occur in an overlapping fashion.

The process starts in S402 where a substrate, such as a silicon wafer or a metallic sheet is prepared, i.e., formed, cleaned and so on. In S404, an intermediate layer, such as the hexagonal boron nitride layer discussed above with respect to FIG. 1, is placed upon the substrate of S402. In S406, a sensing layer, such as one or more layers of molecule-thick graphene, can be directly or indirectly placed atop the substrate of S402.

In varying examples, one could use copper with a (1,1,1) crystal orientation to deposit a hexagonal boron nitride layer in a correct, single crystal orientation, upon which the graphene is deposited in the optimum crystal structure. The copper then can be used as part of a capacitance circuit, with the HBN as the insulator. Such a configuration would be useful if capacitance were used as a sensing mechanism.

In other varying examples when graphene is to be use to detect resistance change, graphene (which is generally highly conductive) can be placed on an insulating material. Silicon dioxide is a viable insulating material for the intermediate layer 120, but given that graphene and hexagonal boron nitride have a common hexagonal structure, hexagonal boron nitride tends to be a more suitable material when graphene is used as a sensing layer. Also, given that there is an extra resistance at each crystal boundary, a single crystalline orientation can produce better results than non-single crystalline embodiments. Therefore, when resistance is used as a detection mechanism, the best results may be attained if a metallic base of a single crystal orientation is used upon which to deposit the other materials. Copper and gold can be purchased in single crystals of predetermined orientation. The process continues to S408.

Steps/operations S408-S418 describe one method of forming sockets in a sensing layer appropriate to target substances. Steps/operations S408-S418 are meant to convey a single non-limiting example that may be replaced by other approaches, such as micro-stamping, depending on any number of factors, such as economics, reliability, the type of target substance, and so on.

In S408 any of various grid placement and orientation steps may be applied in conjunction with molecular placement to the sensing layer. Among which is the imposition of a rectangular interference grid of ultraviolet light on the graphene/sensing surface. The spots of positive interference are relatively thermally hot, and as a result target substances will not adsorb at such locations. Where there is negative interference, however, the graphene/sensing surface stays relatively cool, and target substance adsorb onto the graphene/sensing surface. A magnetic field and/or molecular tethers may optionally be applied to orient individual target substances, if common orientation is desired. Control continues to step S410.

In S410 first socket members tailored to the target substance(s) are placed and absorbed into or onto the sensing layer such that sockets can be built around the target substances without encountering other sockets or target substances, with the excess then removed. Next, in S412, the target substance(s) are deposited onto the sensing layer, with the excess then removed. Control continues to S414.

In S414 chemical precursors to second socket member is deposited onto the sensing layer, with the excess removed, and in S416 chemical reactions are preformed on the precursors to complete socket creation. Control continues to S418.

In S418, once the sockets are completed, the graphene/sensing surface is heated sufficiently to release the target substances from the sockets, but not enough to release the socket members from the graphene/sensing surface. Van der Waals forces between sockets and target substances act as tethers. It is important that socket members adhere to the graphene/sensing surface, and to each other, more strongly than they adhere to the target substance, so the target substances can be released from the sockets without destroying the sockets.

In S420, an appropriate set of post-processing steps can be performed, such as other cleaning, drying and cutting. In S422, individual sensors can be paired with appropriate reference devices, which as stated above can take the form of a device formed according to FIG. 3 (without sockets), or an identical sensor with its sockets sealed to prevent exposure to target substances. Finally, in S424 an appropriate set of signal processing steps can be performed using the sensor and reference device to determine whether or not the sensor has been exposed to the target substance.

While the invention has been described in conjunction with the specific embodiments thereof that are proposed as examples, it is evident that many alternatives, modifications, and variations will be apparent to those skilled in the art. Accordingly, embodiments of the invention as set forth herein are intended to be illustrative, not limiting. There are changes that may be made without departing from the scope of the invention.

What is claimed is:

1. A detection system for detecting the presence of a target substance, comprising:
   a nanosensor having a sensing layer that includes graphene; and
   a plurality of sockets either embedded within the body of the sensing layer or placed directly atop of the sensing layer, wherein each socket includes a plurality of socket members and each socket has a physical profile matching a size and shape of at least a portion of the target substance such that, when target substances occupy the sockets, at least one measurable physical characteristic of the sensing layer changes.

2. The detection system of claim 1, wherein each socket further includes one or more polar elements located so as to improve selectivity of the target substance to the socket.

3. The detection system of claim 2, wherein the sensor further comprises:
   a substrate; and
   an intermediate layer formed upon the substrate, wherein the sensing layer is formed directly upon the intermediate layer.

4. The detection system of claim 2, wherein the sensor further comprises:
   a substrate; wherein the sensing layer is formed directly or indirectly upon the substrate.

5. The detection system of claim 2, wherein the sensing layer is formed from a conductive or semi-conductive material.

6. The detection system of claim 5, wherein the sensing layer is composed of one or more single-atom thick sheets of graphene.

7. The detection system of claim 1, further comprising:
   a reference device paired to the nanosensor so as to share common physical traits as the sensing layer with an exception that the reference device is not susceptible to detecting the target substance; and
   processing circuitry configured to detect physical changes of the sensor and the reference device such that, when measured physical differences occur between the sensor and the reference device, the processing circuitry signals the presence of the target substance.

* * * * *